US007087721B2

(12) United States Patent
Wu et al.

(10) Patent No.: US 7,087,721 B2
(45) Date of Patent: Aug. 8, 2006

(54) COMPOSITIONS, KITS AND TREATING METHODS FOR ALTERATION CELL-CELL ADHESION, TRANSPORT, OR PERMEATION PROPERTIES OF TISSUES

(76) Inventors: Hua-Lin Wu, Department of Biochemistry, College of Medicine, National Cheng Kung University, 1 University Road, Tainan (TW) 701; Guey-Yueh Shi, Department of Biochemistry, College of Medicine, National Cheng Kung University, 1 University Road, Tainan (TW) 701; Huey-Chun Huang, Department of Biochemistry, College of Medicine, National Cheng Kung University, 1 University Road, Tainan (TW) 701

( * ) Notice: Subject to any disclaimer, the term of this patent is extended or adjusted under 35 U.S.C. 154(b) by 0 days.

(21) Appl. No.: 10/938,183

(22) Filed: Sep. 10, 2004

(65) Prior Publication Data

US 2005/0106135 A1 May 19, 2005

Related U.S. Application Data

(60) Provisional application No. 60/503,129, filed on Sep. 15, 2003.

(51) Int. Cl.
 *A61K 35/14* (2006.01)
 *C07K 14/00* (2006.01)
(52) U.S. Cl. .................... 530/381; 530/395; 530/350
(58) Field of Classification Search ................ 530/381, 530/395, 350
See application file for complete search history.

(56) References Cited

U.S. PATENT DOCUMENTS 5,639,625 A * 6/1997 Carson et al. ............. 435/7.92

OTHER PUBLICATIONS

Huey-Chung Huang, et al., "Thrombomodulin-mediated Cell Adhesion", *The Journal of Biological Chemistry*, vol. 278, No. 47, Issue of Nov. 21, pp. 46750-46759, 2003.
C. T. Esmon, et al., "Complex Formation between Thrombin and Thrombomodulin Inhibits Both Thrombin-catalyzed Fibrin Formation and Factor V Activation", *The Journal of Biological Chemistry*, vol. 257, No. 14, Issue of Jul. 25, pp. 7944-7947, 1982.
C. T. Esmon, "Thrombomodulin as a Model of Molecular Mechanisms that Modulate Protease Specificity and Function at the Vessel Surface", *The FASEB Journal*, 946, vol. 9, Jul. 1995.
M. C. Boffa, et al., "Preservation of Thrombomodulin Antigen on Vascular and Estravascular Surfaces", *The Journal of Histochemistry and Cytochemistry*, vol. 35, No. 11, pp. 1267-1276, 1987.

A. M. Healy, et al., "Absence of the Blood-Clotting Regulator Thrombomodulin Causes Embryonic Lethality in Mice Before Development of a Functional Cardiovascular System", *Proc. Natl. Acad. Sci.*, USA, vol. 92, pp. 850-854, Jan. 1995.
T. J. Raise, et al, "Keratinocyte-Specific Expression of Human Thrombomodulin in Transgenic Mice: Effects of Epidermal Differentiation and Cataneous Wound Healing", *Journal of Investigative Medicine*, vol. 46, No. 4, Apr. 1998.
D. A. Lane, et al., "Role of Hemostatic Gene Polymorphisms in Venous and Arterial Thrombotic Disease", *Blood*, Mar. 1, 2000, vol. 95, No. 5, pp. 1517-1532.
Y. Tezuka et al., "Expression of Thrombomodulin in Esophageal Squamous Cell Carcinoma and Its Relationship to Lymph Node Metastasis", *Cancer Reseach*, 55, 4196-4200, Sep. 15, 1995.
T. M. Sugihara, et al., "An Immunohistochemical Study of Thrombomodulin in Oral Squamous Cell Carcinoma and its Association with Invasive amd Metastatic Potential", *J. Oral Pathol Med*, 1997: 26: 258-264.
T. Suehiro et al., "Thrombomodulin Inhibits Intrahepatic Spread in Human Heptocellular Carcinoma", *Hepatology*, May 1995, pp. 1285-1290.
Youming Zhang, et al., "Thrombomodulin Modulates Growth of Tumor Cells Independent of its Anticoagulant Activity", *Thrombomodulin Modulates Tumor Growths*, pp. 1301-1309.
K. Suzuki, et al., "Structure and Expression of Human Thrombomodulin, a Thrombin Receptor on Endothelium Acting as a Cofactor for Protein C Activation", *The EMBO Journal*, vol. 6, No. 7, pp. 1891-1897, 1987.
T. E. Petersen, "The Amino-Terminal Domain of Thrombomodulin and Pancreatic Stone Protein are Homologous with Lectins", *FEB Letters*, vol. 231, No. 1, pp. 51-53, Apr. 1988.
C. H. Chay, et al., "Evidence for Lectin Signaling to the Nuclear Matrix: Cellular Interpretation of the Glycocode", *Journal of Cellular Biochemistry Supplemental*, 35:123-129 (2000).

(Continued)

*Primary Examiner*—Jon Weber
*Assistant Examiner*—Suzanne M. Noakes
(74) *Attorney, Agent, or Firm*—Cohen, Pontani, Lieberman & Pavane

(57) ABSTRACT

The present invention relates to compositions, kits and treating methods for the alteration cell-cell adhesion, transport, or permeation properties of tissues. The present invention also relates to the application of drug(s) or peptide(s), compound or gene delivery, DNA or RNA(i), cosmetic or therapeutic use of the compositions and kits.

5 Claims, 9 Drawing Sheets

OTHER PUBLICATIONS

R. Mody, et al., "Use of Lectins as Diagnostic and Therapeutic Tools for Cancer", *Journal of Pharmacological and Toxicological Methods*, 33, pp. 1-10 (1995).

L. LaRue, et al., "E-Cadherin Null Mutant Embryos Fail to Form a Trophectoderm Epithelium", *Proc. Natl. Acad. Sci.*, vol. 91, pp. 8263-8267, Aug. 1994.

D. Tiethmacher, et al., "A Targeted Mutation in the Mouse E-Cadherin Gene Results in Defective Preimplantation Development", *Proc. Natl. Acad. Sci.*, vol. 92, pp. 855-859, Jan. 1995.

R. O. Hynes, et al., "Perspective Series: Cell Adhesion in Vascular Biology" *Genetic Manipulation of Vascular Adhesion Molecules in Mice*, pp. 2193-2195.

H. Ogawa, et al., "Expression of Thrombomodulin in Squamous Cell Carcinoma of the Lung: Its Relationship to Lymph Node Metastasis and Prognosis of the Patients", *Cancer Letters*, 149 (2000) pp. 95-103.

T. J. Raife, et al., "Thrombomodulin Expression by Human Keratinocytes", *Keratinocyte Thrombomodulin*, pp. 1846-1851.

Y. Matsushita, et al., "A Subcloned Human Esophageal Squamous Cell Carcinoma Cell Line with Low Thrombomodulin Expression Showed Increased Invasiveness Compared with a High Thrombomodulin-Expressing Clone—Thrombomodulin as a Possible Candidate for an Adhesion Molecule of Squamous Cell Carcinoma", *Cancer Letters*, 127 (1998) pp. 195-201.

D. J. Lager et al., "Cellular Localization of Thrombomodulin in Human Epithelium and Squamous Malignancies", *American Journal of Pathology*, vol. 146, No. 4, Apr. 1995.

M. Takeichi, "Cadherin Cell Adhesion Receptors as a Morphogenetic Regular", *Science*, vol. 25, pp. 1451-1455, Mar. 22, 1991.

M. Conacci-Sorrell, et al., "The Cadherin-Catenin Adhesion System in Signaling and Cancer", *The Journal of Clinical Investigation*, Apr. 1002, vol. 109, No. 8, pp. 987-991.

P. Boukamp, et al., "Normal Keratinization in a Spontaneously Immortalized Aneuploid Human Keratinocyte Cell Line", *The Journal of Cell Biology*, vol. 106, 1988, pp. 761-771.

B. Herren, et al., "ADAM15 Overexpression in NIH3T3 Cells Enhances Cell-Cell Interactions", *Experimental Cell Research*, 271, 152-160 (2001).

M. S. Kinch, et al., "Tyrosine Phosphorylation Regulates the Adhesions of Ras-Transformed Breast Epithelia", *The Journal of Cell Biology*, vol. 130, 1995, pp. 461-471.

M. Pignatelli, et al., "Morphoregulatory Activities of E-Cadherin and beta-1 Integrins in Colorectal Tumor Cells", *Br. J. Cancer*, (1992), 66, pp. 629-634.

H. Togashi, et al., "Cadherin Regulates Dendritic Spine Morphogenesis", *Neuron*, vol. 35, pp. 77-89, Jul. 3, 2002.

E. M. Conway, et al., "The Amino Terminal Lectin-Like Domain of Thrombomodulin is Required for Constitutive Endocytosis", *Blood*, vol. 89, No. 2, 1997, pp. 652-661.

E. M. Conway, et al., "The Lectin-Like Domain of Thrombomodulin Confers Protection from Neutrophil-Mediated Tissue Damage by Suppressing Adhesion Molecule Expression Via Nuclear Factor κB and Mitogen-Activated Protein Kinase Pathways", *J. Exp. Med.*, vol. 196, No. 5, Sep. 2, 2002, pp. 565-577.

S. Hirano, et al., "Calcium-Dependent Cell-Cell Adhesion Molecules (Cadherins): Subclass Specificities and Possible Involvement of Actin Bundles", *The Journal of Cell Biology*, vol. 105 (No. 6, Pt. 1), Dec. 1987, pp. 2501-2510.

A. Hubbard, et al., "Intercellular Adhesion Molecule-1 (ICAM-1) Expression and Cell Signling Cascades", *Free Radical Biology & Medicine*, vol. 28, No. 9, pp. 1379-1386, 2000.

S. D. Rosen, et al., "Ligands for L-Selectin: Homing, Inflammation, and Beyond", *Annu. Rev. Immunol.* 2004, 22:129-156.

A. Varki, et al., "P-Selectin, Carcinoma Metastasis and Heparin: Novel Mechanistic Connections with Therapeutic Implications", *Brazilian Journal of Medical and Biological Research*, 2001, 34: 711-717.

P. D. Stahl, "The Mannose Receptor and Other Macrophage Lectins", *Current Opinion in Immunology*, 1992, 4:49-52.

K. Nawa, et al., "Presence and Function of Chondroitin-4-Sulfate on Recombinant Human Soluble Thrombomodulin", *Biochemical and Biophysical Research Communication*, pp. 729-737.

L. Pollack et al., "Correlation of Glycosylation Forms with Position in Amino Acid Sequence", *The Journal of Cell Biology*, vol. 97, Aug. 1983, 293-300.

S. Pokutta et al., "The Cytoplasmic Face of Cell Contact Sites", *Current Opinion in Structural Biology*, 2002, 12:255-262.

E. M. Conway, et al. "Structure-Function Analyses of Thrombomodulin by Gene-Targeting in Mice: The Cytoplasmic Domain is not Required for Normal Fetal Development", *Blood*, vol. 93, No. 10, May 15, 1999, pp. 3442-3450.

N. G. Ordóñez, "Transitional Cell Carcinomas of the Ovary and Bladder are Immunophenotypically Different", *Histopathology*, 2000, 36, 433-438.

\* cited by examiner

A

B

C

COMPOSITIONS, KITS AND TREATING METHODS FOR ALTERATION CELL-CELL ADHESION, TRANSPORT, OR PERMEATION PROPERTIES OF TISSUES

RELATED APPLICATIONS

This application claims priority from U.S. Provisional Patent Application Ser. No. 60/503,129 which was filed on Sep. 15, 2003.

BACKGROUND OF THE INVENTION

Field of the Invention

The present invention relates to compositions, kits and treating methods for the alteration cell-cell adhesion and permeation properties of tissues. The present invention also relates to the application of drug, compound or gene delivery, cosmetic or therapeutic use of the compositions and kits.

Thrombomodulin (TM) is a membrane-intercalated glycoprotein, which functions in anticoagulation by virtue of complexation with thrombin. The complex can effectively activate protein C, that in turn catalyzes the proteolytic inactivation of blood coagulation factors Va and VIIIa, leading to down-regulation of the blood coagulation cascade (Esmon, C. T. et al., (1982) *J. Biol. Chem* 257, 7944–7947 and Esmon, C. T. (1995) *FASEB J* 9, 946–955). TM is constitutively expressed on endothelial cells (Esmon, C. T. et al., (1982) *J. Biol. Chem* 257, 7944–7947). As such, it might be one of the factors that localizes the coagulation cascade to sites of vascular injury (Esmon, C. T. (1995) *FASEB J* 9, 946–955).

The observations from a number of studies support the contention that TM may also play a role in other extravascular activities (Boffa, M. C. et al., (1995) *J. Histochem. Cytochem.* 35, 1267–1276).

Ablation of the TM gene causes early post-implantation embryonic lethality that precedes the establishment of a functional cardiovascular system (Healy, A. M. et al., (1995) *Proc. Natl. Acad. Sci. USA.* 92, 850–854). TM may also have antiscarring properties, by virtue of the modulation of early collagen deposition of normal epidermis (Raife, T. J., (1998) *J. Investig. Med.* 46, 127–133). Complete or near complete TM-deficiency has not been reported in humans (Lane, D. A. (2000) *Blood* 95, 1517–1532), which is consistent with the view that a severe reduction of TM function may have more dire consequences than the defects in coagulant or anticoagulant factors.

An inverse correlation between TM expression and tumor progression is evident clinically (Tezuka Y. et al., (1995) *Cancer Res.* 55, 4196–4200; Tabata, M., et al., (1997) *J. Oral. Pathol. Med.* 26, 258–264 and Suehiro, T., et al., (1995) *Hepatology* 21, 1285–1290). It was demonstrated that TM exerted a growth suppressing effect independent of its anticoagulant activity, but dependent on the lectin-like domain (Zhang Y., et al., (1998) *J. Clin. Invest.* 101, 1301–1309).

The myriad and diverse possible functions of TM may reflect the glycoprotein structure. TM consists of 557 amino acid residues arranged in five distinct domains: an $NH_2$-terminal lectin-like domain, a domain with six epidermal growth factor (EGF)-like structures that contain thrombin binding sites, an O-glycosylation site-rich domain, a transmembrane domain, and a cytoplasmic tail (Suzuki, K. et al., (1987), *EMBO J.* 6, 1891–1897). The $NH_2$-terminal lectin-like domain has two modules. The first 155 amino acid module, is homologous to $Ca^{2+}$-dependent lectin (Petersen, T. E. (1988) *FEBS Lett.* 231, 51–53).

The second module, adjacent to the EGF-like domain, is a hydrophobic region of 70 amino acid residues. These lectin-like domains exist in other proteins, where they participate in a wide variety of cell biologic processes, including inflammation and cell-to-cell recognition processes (Chay, C. H. et. al., (2000) *J. Cell Biochem. Suppl.* 35, 123–129; Mody, R. et al., (1995) *J. Pharmaco. Toxicol. Meth.* 33, 1–10). The TM lectin-like domain is not required for cofactor activity for activating protein C, and its biological function remains mostly unclear. It has been reported that many null mutations in adhesion genes are lethal during embryonic development (Larue, L., et al., (1994) *Proc. Natl. Acad. Sci. USA.* 91, 8263–8267; Riethmacher, D., et. al., (1995) *Proc. Natl. Acad. Sci. USA.* 92, 855–859 and Hynes, R. O. et. al., (1996) *J. Clin. Invest.* 98, 2193–2195), and that TM is necessary for embryonic development (Healy, A. M. et al., (1995) *Proc. Natl. Acad. Sci. USA.* 92, 850–854).

The lectin-like activity may be influential in a cell-to-cell adhesive interaction (Ogawa, H. et. al., (2000) *Cancer Lett.* 149, 95–103). It is conceivable that TM may function as an additional cellular adhesive molecule. Immunocytochemical studies have localized the TM antigen principally to the intercellular bridges between keratinocytes in stratified squamous epithelium of skin and in various benign or malignant squamous cell carcinomas (Tezuka Y. et al., (1995) *Cancer Res.* 55, 4196–4200; Raife, T. J. et. al., (1994) *J. Clin. Invest.* 93,1846–1851; Matsushita, Y., et. al., (1998) *Cancer Lett.* 127, 195–201; and Larger, D., J. et. al., (1995) *Am. J. Pathol.* 146, 933–943).

Indeed; the levels of both E-cadherin and TM are decreased in metastases of squamous cell carcinoma (Tezuka Y. et al., (1995) *Cancer Res.* 55, 4196–4200 and Takeichi, M. (1991) *Science* 251, 1451–1455). It is well known that E-cadherin-dependent cell-to-cell adhesion is important for the maintenance of epithelial structural integrity, and that the loss of E-cadherin expression is correlated with increased invasive potential of both carcinoma cell lines and tumor samples (Conacci-Sorrell, M. et. al., (2002) *J. Clin. Invest.* 109, 987–991). The parallel relationship of the expression levels of E-cadherin and TM in tumor progression prompted us to test the adhesion and morphoregulatory activities of TM in comparison with E-cadherin.

Although the direct participation of TM in cell-to-cell adhesion is suspected, no supportive experimental evidence has been provided.

SUMMARY OF THE INVENTION

The invention is provided with a composition comprising thrombomodulin and the substance binding the lectin-like domain of thrombomodulin.

The invention is also provided with a kit for use in sorting or isolating cells comprising the substance binding the lectin-like domain of thrombomodulin.

The invention is further provided with a method of altering cell-to-cell adhesion, said method comprising exposing cells to an effective amount of the substance binding the lectin-like domain of thrombomodulin.

DETAILED DESCRIPTION OF THE PRESENTLY PREFERRED EMBODIMENTS

Figure 1:
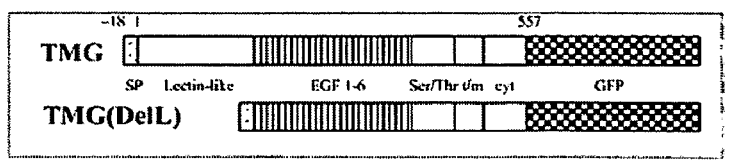
FIG. 1 shows (A) schematic diagram illustrating TMG and TMG(ΔL) constructed in pEGFPN1; (B) TM activity assay of A2058 cells stably expressing TMG and TMG(ΔL), and (C) Characterization of TM proteins by mouse anti-human TM antiserum.
Figure 1:
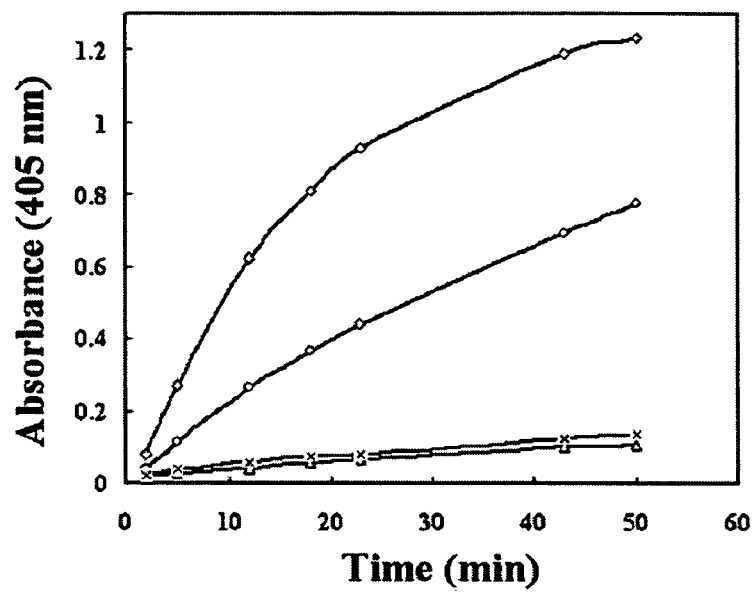
Figure 1:
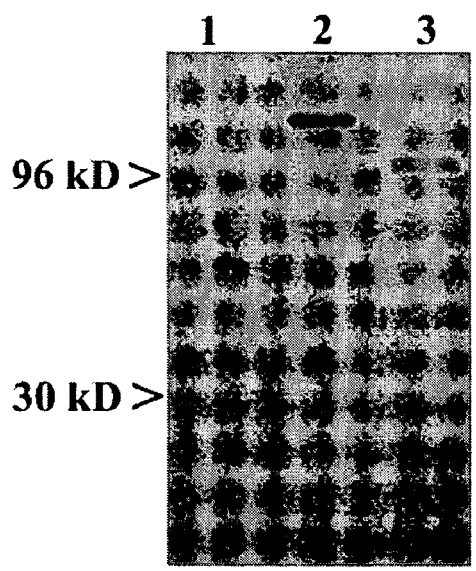

The present study sought such evidence, through the testing of the hypothesis that TM functions as a cell-to-cell adhesion molecule, and, if so, to elucidate the roles of the participating TM domains. In light of the above, there is obvious interest in identifying novel methods and compositions which are useful for diagnosing and treating tumors which are associated with gene amplification.

Clones of A2058 melanoma cells that stably expressed green fluorescent protein (GFP)-tagged full-length or lectin-like domain truncated TM were generated. In the invention, the lectin-like domain of TM prompted the clustering of cells in close proximity with one another by enhancing cell-to-cell adhesiveness through a $Ca^{2+}$-dependent interaction of TM molecules. This interaction could be involved in limiting cell growth.

The present invention is provided with a composition comprising thrombomodulin and the substance binding the lectin-like domain of thrombomodulin. In the composition of the invention, thrombomodulin has function as a $Ca^{2+}$-dependent cell-to-cell adhesion molecule.

The substance binding the lectin-like domain of thrombomodulin is selected from the group consisting of mannose, chondroitin sulfate (such as chondroitin sulfate A, chondroitin sulfate C), oligomer, polymer, analogues, complex molecules containing part of the structure, antibodies, or drugs to alter the cell-to-cell adhesion, transport, or tissue permeability. The preferred substance binding the lectin-like domain of thrombomodulin is selected from the group consisting of mannose, chondroitin sulfate A, chondroitin sulfate C and antibodies against the lectin-like domain of thrombomodulin.

The composition of the invention could be applied to the application of drug, compound or gene delivery, cosmetic or therapeutic use, the alteration of the cell-to-cell adhesion, transport, or tissue permeability.

The present invention is provided with a kit for use in sorting or isolating cells comprising the substance binding the lectin-like domain of thrombomodulin. In particular, the kit of the invention could be used in sorting or isolating keratinocytes isolated from tumors or tissues.

In the kit of the invention, the substance binding the lectin-like domain of thrombomodulin is selected from the group consisting of mannose, chondroitin sulfate (such as chondroitin sulfate A, chondroitin sulfate C), oligomer, polymer, analogues, complex molecules containing part of the structure, antibodies, or drugs to alter the cell-to-cell adhesion, transport, or tissue permeability. The preferred substance binding the lectin-like domain of thrombomodulin is selected from the group consisting of mannose, chondroitin sulfate A, chondroitin sulfate C and antibodies against the lectin-like domain of thrombomodulin.

In the embodiment of the invention, mannose, chondroitin sulfate A or chondroitin sulfate C is coated on culture vessels or solid particles. In the further embodiment of the invention, mannose, chondroitin sulfate A or chondroitin sulfate C is ligated with matrix or solid surface for isolation of thrombomodulin or derivatives thereof.

The present invention is further provided with a method of alterating cell-to-cell adhesion, said method comprising exposing cells to an effective amount of the substance binding the lectin-like domain of thrombomodulin. In particular, the alteration is related to the cell growth or migration rate or morphology of cell culture.

In the method of the invention, the substance binding the lectin-like domain of thrombomodulin is selected from the group consisting of mannose, chondroitin sulfate (such as chondroitin sulfate A, chondroitin sulfate C), oligomer, polymer, analogues, complex molecules containing part of the structure, antibodies, or drugs to alter the cell-to-cell adhesion, transport, or tissue permeability. The preferred substance binding the lectin-like domain of thrombomodulin is selected from the group consisting of mannose, chondroitin sulfate A, chondroitin sulfate C and antibodies against the lectin-like domain of thrombomodulin.

In the preferred embodiment of the method of the invention, the substance binding the lectin-like domain of thrombomodulin in combination with drug. The drug could be combined with EDTA or anti-thrombomodulin antibodies.

The method of the invention could be applied to the use of drug delivery to tumors of tissues such as those from skin, epithelial, mucous membrane of oral cavity, nasal cavities, stomach, intestine or genital organs. In the preferred embodiment of the method of the invention, the tumors are squamous cell carcinoma or cervical cancer.

The following examples are offered for illustrative purposes only, and are not intended to limit the scope of the present invention in any way.

All patent and literature references cited in the present specification are hereby incorporated by reference in their entirety.

EXAMPLES

Example 1

Materials

Tissue culture dishes and plastic ware were purchased from Corning Life Sciences (Corning, N.Y.). Lipofectin and cell culture reagents were from Gibco-BRL (Gaithersburg, Md.). Restriction enzymes used in DNA manipulation were purchased from New England Biolabs (Beverly, Mass.) or Promega Corporation (Madison, Wis.). The pEGFPN1 vector was from BD Biosciences Clontech (Palo Alto, Calif.). Monoclonal mouse antibody to the EGF5–EGF6 domain of TM IgG1antibody and Chromozym PCa were purchased from American Diagnostica Inc (Greenwich, Conn.). Human protein C, antithrombin III, G418 (neomycin) and anti-human E-cadherin antibody (clone HECD-1) were from Calbiochem-Novabiochem Corporation (San Diego, Calif.). Monoclonal anti-lectin-like domain antibody (clone D-3), isotype control IgG antibody, tetramethylrhodamine conjugated phalloidin, and goat anti-human keratin antibody were obtained from Santa Cruz Biotechnology, Inc (Santa Cruz, Calif.). Tetramethylrhodamine goat anti-mouse IgG, and tetramethylrhodamine rabbit anti-goat antibody were purchased from Molecular Probes (Eugene, Oreg.). Supersignal enhanced chemiluminescence (ECL) reagent was obtained from Pierce Biotechnology, Inc. (Rockford, Ill.). D-mannose, D-galactose, D-lactose, D-glucose, D-xylose, heparin, low molecular weight heparin (LMW heparin), chondroitin sulfate A, chondroitin sulfate B and chondroitin sulfate C were from Sigma-Aldrich (St. Louis, Mo.). All other chemicals were of the highest grade commercially available.

Construction of Green Fluorescent Protein-Tagged Thrombomodulin

Human TM gene in chromosomal DNA was amplified by PCR using a BamHI forward primer, TM719 (5'-CGGGATCCCGGAATGCTTGGGGTCCTGGTCCTTG-3') (SEQ ID NO: 1) and an EcoRI reverse primer (5'-GGAATTCGGAGTCTCTGCGGCGTCCGCT-3') (SEQ ID NO: 2). The 1.7 kb PCR product encoding amino acid residues 1–575 was digested with BamHI and EcoRI. The resulting fragment was ligated to the expression vector pEGFPN1, which had been digested with BglII and EcoRI. This construct was named TMG. The lectin-like module within the $NH_2$-terminal domain of TM was removed by recombinant PCR using the following method. Four primers were designed such that they overlapped and skipped the lectin-like module. Two oligonucleotide primers, TM719 and TM1480 (5'-CATTGCACGCGTGCTCGCAGCCGC-3') (SEQ ID NO: 3) flanked the region from nucleotide 719 to 1480. The other primers were (5'-CACGCTGCAGTCCCAAGCGCCACCCGGCTGCGGCTC-3') (SEQ ID NO: 4) and its reverse complement (5 '-GAGCCGCAGCCGGGTGGCGCTTGGGACTGCAGCGTG-3 ')SEQ ID NO: 5). Each of the latter two primers was utilized with primer TM719 and TM1480 for PCR amplifications, respectively. The 92 and 66 bp PCR products were purified, denatured, annealed, and amplified using primers TM719 and TM1480. The recombinant 140 bp product was digested with BamHI and MluI, and subcloned to replace the wild type $NH_2$-terminal domain of human TM in the expression vector pEGFPN1. The final product was designated TMG (ΔL). Both constructs were confirmed by DNA sequencing.

Cell Culture and Transfection of Human Melanoma (A2058) Cells

A2058 cells (ATCC CRL-11147) or HaCaT cells (Boukamp, P. et. al., (1988) *J. Cell Biol.* 106, 761–771) were maintained in Dulbecco's Modified Eagle Medium (DMEM) supplemented with 0.292 g/L L-glutamine and 10% fetal bovine serum (FBS). A2058 cells grown until 40–60% confluence were transfected with TMG or TMG (ΔL) using lipofectin reagent. To generate cell lines stably expressing the various constructs, cells were diluted and seeded two days after transfection and maintained in DMEM supplemented with 400 µg/ml G418 (neomycin). Clonal expression was examined initially by fluorescence microscopy, and clones for further study were selected and expanded.

Thrombomodulin Activity Assay

Cells at a density of $2 \times 10^4$/well were split into wells of a 96-well plate and allowed to reattach overnight. The cells were washed in a buffer containing 20 mM Tris (pH 7.4), 0.15 M NaCl, 2.5 mM $CaCl_2$, and 5 mg/ml bovine serum albumin (BSA) and incubated with 40 µl reaction mixture (37.5 nM thrombin and 5 µg/ml protein C in the washing buffer) at 37° C. for 30 min. Protein C activation was terminated by adding 40 µl antithrombin III (6 IU/ml) and heparin (12 IU/ml). The enzymatic activity of activated protein C was measured with the peptide substrate H-D-Lys-Z-Pro-Arg-4-nitroanilide-diacetate (Chromozym PCa; 0.5 mM in 20 mM Tris, pH 7.4, 0.15 M NaCl, and 5 mg/ml BSA) at 37° C. The absorbance change at 405 nm was measured with a Thermomax Microplate Reader (Molecular Devices Corporation, Sunnyvale, Calif.). Controls containing thrombin and protein C in the absence of cells were treated similarly.

Electrophoresis and Immunoblot Analyses

TM-expressing cells were washed twice with cold phosphate-buffered saline (PBS), lysed in PBS containing 1% (v/v) Nonidet P-40, 0.5% (w/v) sodium deoxycholate, 0.1% (w/v) sodium dodecyl sulfate (SDS), 5 µg/ml aprotinin, 100 µg/ml phenylmethylsulfonyl fluoride, 1 pg/ml pepstatin A, and 1 mM ethylenediaminetetraacetic acid at 4° C. for 20 min, and then disrupted with a needle. Total lysates were quantified using microBCA kit (Pierce). Proteins (10 µg) were resolved by SDS-polyacrylamide gel electrophoresis and transferred electrophoretically to a nylon filter. The nylon filter was blocked for 1 h in 5% (v/v) fat-free milk in PBST buffer (PBS with 0.05% Tween-20). After a brief wash in the buffer, the nylon filter was incubated overnight at 4° C. with mouse anti-human TM antiserum diluted in PBST buffer. The antiserum was prepared in our laboratory from BALB/c mice immunized with recombinant TM protein purified from the *Pichia pastoris* expression system. The primary antibody was removed, and the filter was washed four times in PBST buffer. Subsequent incubation with horseradish peroxidase-labeled goat anti-mouse antibody proceeded at room temperature for 2 h. The filter was washed four times in PBST buffer to remove the secondary antibody, and the blot was visualized with ECL reagent.

Confocal Microscopy

To examine the distribution of TM, transfected cells were grown on poly-lysine coated coverslips overnight. The coverslips were washed three times with cold PBS, and the cells were fixed with a 3.7% (v/v) formaldehyde solution in PBS and mounted with Vectashield mounting medium (Vector Lab Inc., Burlingame, Calif.). Cells were observed using a laser scanning confocal microscope (Leica Model TCS2) with a Leica Mellis-Griot 63X NA oil immersion objective, pinhole of 1.5, and electronic zoom 1.5 or 2. Green fluorescent protein (GFP) was excited using a 488 nm argon/krypton laser and detected with 515–540 nm band pass filter. Tetramethylrhodamine was excited using a 543 nm argon/krypton laser and detected with 550–620 nm band pass filter. The images were manipulated with a Leica TCS NT scanner.

Immunofluorescence Staining

For immunofluorescence staining, cells were grown on glass coverslips at 37° C. Following fixed in 3.7% (v/v) formaldehyde in PBS, cells were permeabilized with 0.2% (v/v) Triton X-100 and blocked with 10% FBS in PBS.

Tetramethylrhodamine-phalloidin, anti-keratin antibody, anti-lectin-like domain antibody, or anti-human TM EGF-like domain antibody was applied to the samples. After three PBS washes, cells were incubated for 1 h at room temperature with tetramethylrhodamine-labeled secondary antibodies. Glass coverslips were washed three times with PBS, mounted, and examined using a confocal microscope.

Calcium-Switch Methods

Cells were grown overnight on glass coverslips at a constant density ($5 \times 10^4$ cells/well) in 24 well culture plates. The cells were serum-starved for 8 h and $Ca^{2+}$ was removed by incubation with DMEM medium containing 4 mM ethyleneglycol-bis-(Amino-Ethyl-Ether) N,N,N',N'-tetraacetic acid (EGTA) and 1 mM $MgCl_2$ at 37° C. After 1 h, the DMEM medium containing 1.8 mM $Ca^{2+}$ was added to replace the $Ca^{2+}$-free medium. In control experiments, cells received fresh media in the absence of EGTA. In selected experiments, 10 μg/ml of anti-TM lectin-like antibody, 10 μg/ml of isotype-specific control antibody or anti-E-cadherin antibody (20 μg/ml) was added to the $Ca^{2+}$-containing medium.

Determination of Carbohydrate Specificity for TM-Mediated Cell Adhesion

A variety of simple carbohydrate (D-mannose, D-galactose, D-lactose, D-glucose, D-xylose), heparin, LMW heparin, chondroitin sulfate A, chondroitin sulfate B, and chondroitin sulfate C were tested to determine their ability to block cell-cell adhesion of the TMG cells. In these experiments, the carbohydrate to be tested was added to the cell monolayer to compare its ability to compete with the TMG. The plates were then incubated at 37° C. for overnight and examined by light microscopy (Leica Model DM IL).

Monolayer Permeability Assay

Horseradish peroxidase (HRP) flux across A2058 cells monolayers was measured using Transwell cell culture chambers (0.4 μm-pore polycarbonate filters; Corning, N.Y.) as previously described (Herren, B. (2001) *Exp. Cell Res.* 271, 152–160). Briefly, A2058 cells ($7.5 \times 10^4$) were cultured for 2 to 3 d in Transwell units (Corning). After reaching confluency, cells were washed and the medium was replaced with serum-free medium (1.5 ml upper chamber and 2.6 ml lower chamber). Type IV-A HRP (0.1 μM) was added to the upper chamber and incubated at 37° C. At the indicated time, medium in the lower chambers was assayed for HRP activity using a 2,2'-azino-bis(3-ethylbenzthiazoline-6-sulfonic acid) liquid substrate system according to the manufacture's instructions (Sigma Chemical Co.).

Tumor Growth in Vivo

For study the in vivo growth of A2058 cells, BALB/c SCID male mice were used. Cells ($10^6$) in 100 μl PBS were injected subcutaneously into 6 to 8 week old male mice. Tumor sizes were recorded every 7 d by measuring two largest diameters.

Results

Expression of TMG and TMG(ΔL) Proteins in A2058 Cells

The cDNA encoding either the full-length human TM or the lectin-like domain truncated TM was cloned from human DNA and ligated to the GFP gene in the mammalian expression vector pEGFPN1 (FIG. 1A). Each recombinant gene was transfected into A2058 cells. Several stable clones expressing TM-GFP fusion proteins were initially screened by the presence of GFP auto-fluorescence on the cell membrane. These clones (TMG and TMG(ΔL)) were maintained for the experiments described subsequently. The thrombin interacting domain of TM extended to the outer surface of the cells (as expected in native TM) because the cells expressing TMG or TMG(ΔL) proteins activated protein C in conjunction with thrombin, whereas clones that expressed GFP alone showed no thrombin-dependent protein C activation (FIG. 1B). The TMG and TMG(ΔL) proteins had molecular masses of 110 kDa and 94 kDa, respectively, which were close to the calculated values (FIG. 1C).

TM Localization and Cell Morphology

Figure 2:
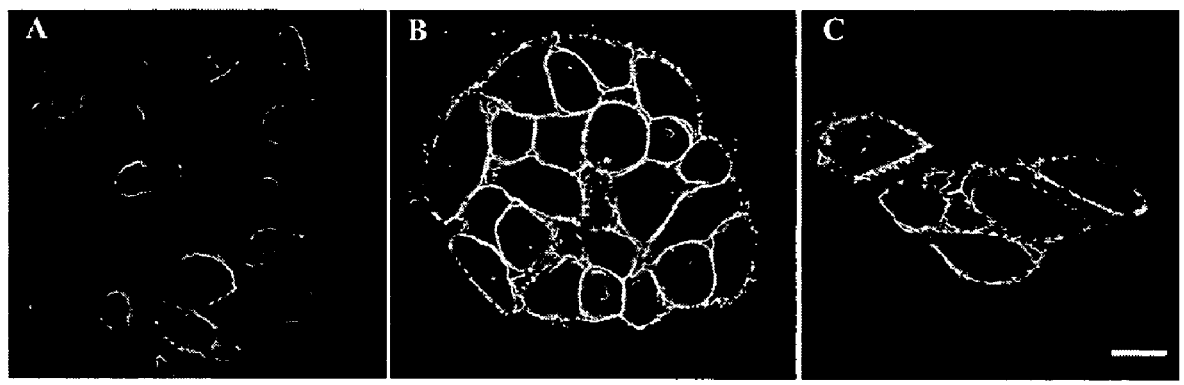
FIG. 2 shows confocal microscopy examination of the subcellular distribution of TM proteins in A2058 cells and the cell morphology.

The cell morphology and subcellular localization of GFP-tagged TM protein in A2058 cells were monitored by confocal microscopy. The green fluorescence of the GFP-expressed cells was evident in the cytoplasm, with a higher concentration in the nuclear region (FIG. 2A). Conversely, the green fluorescence of TMG proteins was distributed near the cell surface, particularly at regions of cell-to-cell contact (FIG. 2B). The fluorescence of TMG(ΔL) was evenly distributed on the cell membrane (FIG. 2C). The cells expressing TMG clustered closely together, with strong cell-to-cell adhesion that was distinctly different from parental A2058 cells and cells expressing GFP or TMG(ΔL) (FIG. 2). Phase contrast images also showed that cells expressing TMG produced compact cell colonies, and cells at the edges of colonies rarely extended membrane protrusions onto the surrounding cell-free surface (FIG. 3A). In contrast, both the clones of the GFP- or TMG(ΔL)-expressed cells were poorly compacted and had a more fibroblastic morphology than TMG-expressed cells (FIG. 3A). Similar results were observed in five stable clones of TMG and seven clones of TMG(ΔL).

Lectin-Like Domain Mediated Cell-to-Cell Adhesion

Figure 3:
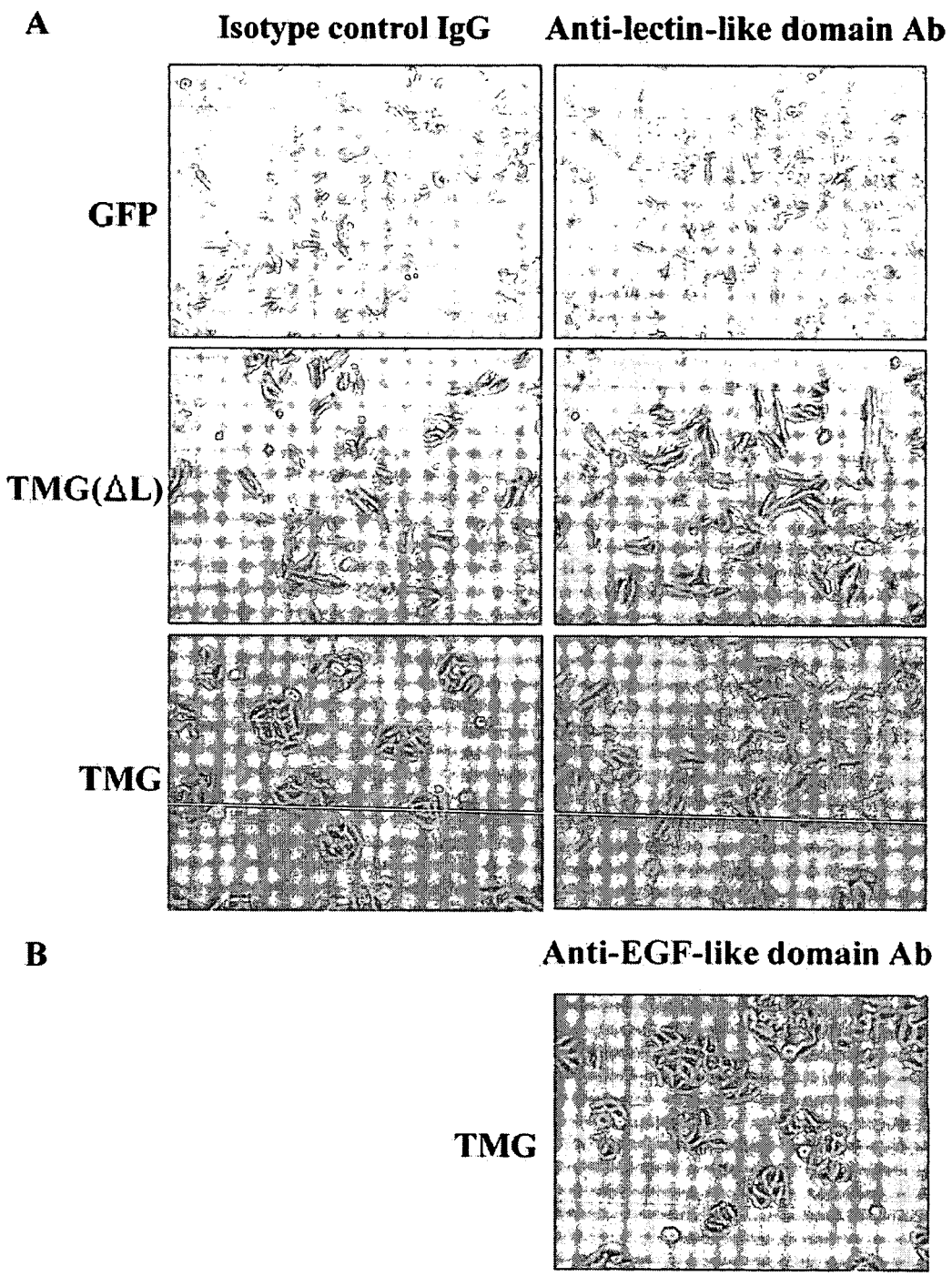
FIG. 3 shows effects of anti-TM antibodies on the organization of cell-cell adhesion junctions in TMG-expressed A2058 cells.
Figure 4:
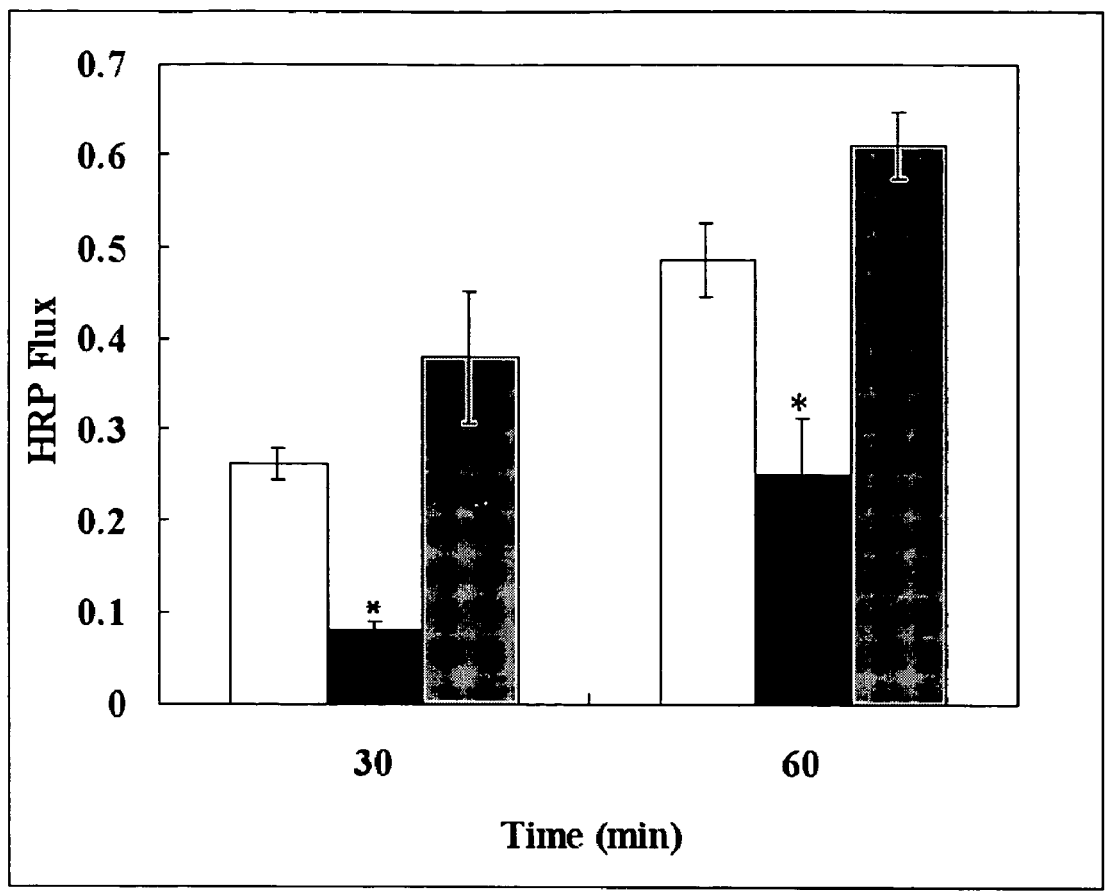
FIG. 4 shows Overexpression of TMG decreases the A2058 cell monolayer permeability.

Because accumulation of TM proteins in the cell-to-cell adhesion sites led to the establishment of the compact clustering morphology, we further explored whether the lectin-like domain of TM played a critical role in cell-to-cell contacts. A monoclonal antibody (Clone D-3) directed against the lectin-like domain was used to block the function of lectin-like domain and to test its effect on cell morphology. The antibody bound specifically to TM protein in the TMG cell lysates, rather than any proteins in the control or TMG(ΔL) cell lysates, as shown by Western blotting results. When the TMG-expressed cells were incubated with a monoclonal antibody directed against the lectin-like domain, the cell-to-cell contacts were completely inhibited (FIG. 3A). On the other hand, the antibody specific for the EGF-like domain of TM did not cause the TMG-expressed cells to assume the dispersed type colony (FIG. 3B). These results were consistent with a more critical role of the lectin-like domain, versus the EGF-like domain, in promoting the formation of close cell-to-cell contacts in the cultures of TMG-expressed cells. To further investigate the effect of TM expression on the permeability of the cell-to-cell junction, the infiltration ability of horseradish peroxidase through a monolayer of the cell cultures on the polycarbonate membrane was measured using a Transwell assay system. The permeability of the monolayer of TMG cell cultures was significantly lower compared to the TMG(ΔL) and control cells (FIG. 4). Previous reports have demonstrated that human keratinocytes express TM, which appears to be predominantly localized to the cell membrane and the intercellular bridges (Raife, T. J. et. al., (1994) *J. Clin. Invest.* 93, 1846–1851). To further verify the potential physiologic importance of TM in the cell-to-cell adhesion junction, a keratinocyte cell line derived from normal human epidermis (HaCaT) (Boukamp, P. et. al., (1988) *J. Cell. Biol.* 106, 761–771), which expressed TM endogenously, was used to observe the morphologic changes in the presence of a monoclonal antibody directed against the lectin-like domain of TM. Immunofluorescence microscopy using an anti-TM lectin-like domain antibody showed that a high concentration of TM protein was localized at the intercellular boundary of HaCaT cells (FIG. 5A). The cultured HaCaT cells showed typical compacted sheet-forming colonies. However, HaCaT cells were almost completely dissociated when cultured in the medium containing the anti-lectin-like domain antibody for 24 h. The anti-EGF domain antibody or the isotype control IgG failed to dissociate the compact colonies (FIGS. 5B–D).

$Ca^{2+}$ Involvement in TM-Mediated Cell-to-Cell Adhesion

The $NH_2$-terminus of the TM molecule contains a C-type lectin domain, to which the binding of potential ligand is $Ca^{2+}$-dependent. The $Ca^{2+}$ switch method was utilized to investigate whether TM-mediated adhesion junction assembly is $Ca^{2+}$-dependent. The cell-to-cell contacts of the A2058TMG (FIG. 6A) or HaCaT (FIG. 6F) cells were disrupted when the culture medium was changed to the EGTA-containing medium for 40 min (FIG. 6B, 6G). The cell-to-cell adhesion junction was restored in the $Ca^{2+}$-containing medium for 1 h with the presence of 10 µg/ml of control IgG (FIG. 6C, 6H). To further verify the TM domain that was directly involved in the $Ca^{2+}$-modulated adhesion, the functional antibody against the lectin-like domain of TM was added to the $Ca^{2+}$-containing medium, following the EGTA dissociation of cell-to-cell adhesion. No restoration of cell-to-cell adhesion occurred in the presence of a 10 µg/ml concentration of the antibody (FIG. 6D, 6I). Furthermore, TM localization became more uniformly distributed rather than concentrated at the intercellular region (FIG. 6I). Anti-E-cadherin antibody (20 µg/ml) was able to inhibit $Ca^{2+}$-dependent cell-cell adhesion in HaCaT cells (FIG. 6J), but not in TMG cells (FIG. 6E).

TMG Colocalized with Actin Filaments at the Submembrane Cortex

The intracellular domains of adhesion molecules, including cadherins and integrins, interact with the cytoskeleton actin filaments or intermediate filaments through adaptor proteins inside the cell. These interactions provide mechanical continuity from cell to cell (Kinch, M. S., et al., (1995) J. Cell. Biol. 130, 461–471). We examined the colocalization of the TMG proteins and these cytoskeletal elements in TMG-expressed cells by confocal microscopy. The actin and intermediate filaments in the cultured cells were immunohistochemically stained with tetramethylrhodamine-labeled phalloidin or anti-human keratin antibody, respectively. The surface TM molecules and actin filaments were colocalized at the cortex region in cell-cell adhesion sites (FIG. 7A). In contrast, the keratin filaments localized in the cytoplasmic region and there was little overlap in distribution between the TM and intermediate filaments (FIG. 7B).

Influence of mannose, chondroitin sulfate A or chondroitin sulfate C on the cell-cell adhesion in TMG cells Based on the observation that TMG-expressed A2058 cells formed close clustering colonies, we proposed that the lectin-like domain of TM might mediate the cell-cell adhesion by binding to specific carbohydrate moieties of the neighboring cells. To test the hypothesis, different carbohydrates, including D-mannose, D-galactose, D-glucose, D-xylose, D-lactose, chondroitin sulfate A, B and C, heparin, and LMW heparin, were tested for their ability to disperse the close clustering morphology of the TMG culture cells. Among these monosaccharides, only mannose was found to be effective in inducing of cell dispersion. Among the sulfate containing polysaccharides, chondroitin sulfate A (chondroitin 4-sulfate) and chondroitin sulfate C (chondroitin 6-sulfate), also could induce cell dispersion. Heparin showed a minor inhibitory effect on the cell adhesion. On the other hand, chondroitin sulfate B (dermatan sulfate) showed no effect. A similar inhibition of the cell-cell adhesion by mannose or chondroitin sulfate C was observed in HaCaT cells whereas the other sugars had no effects.

Influence of the Overexpression of TM on Tumor Cell Growth in Vivo

Figure 9:
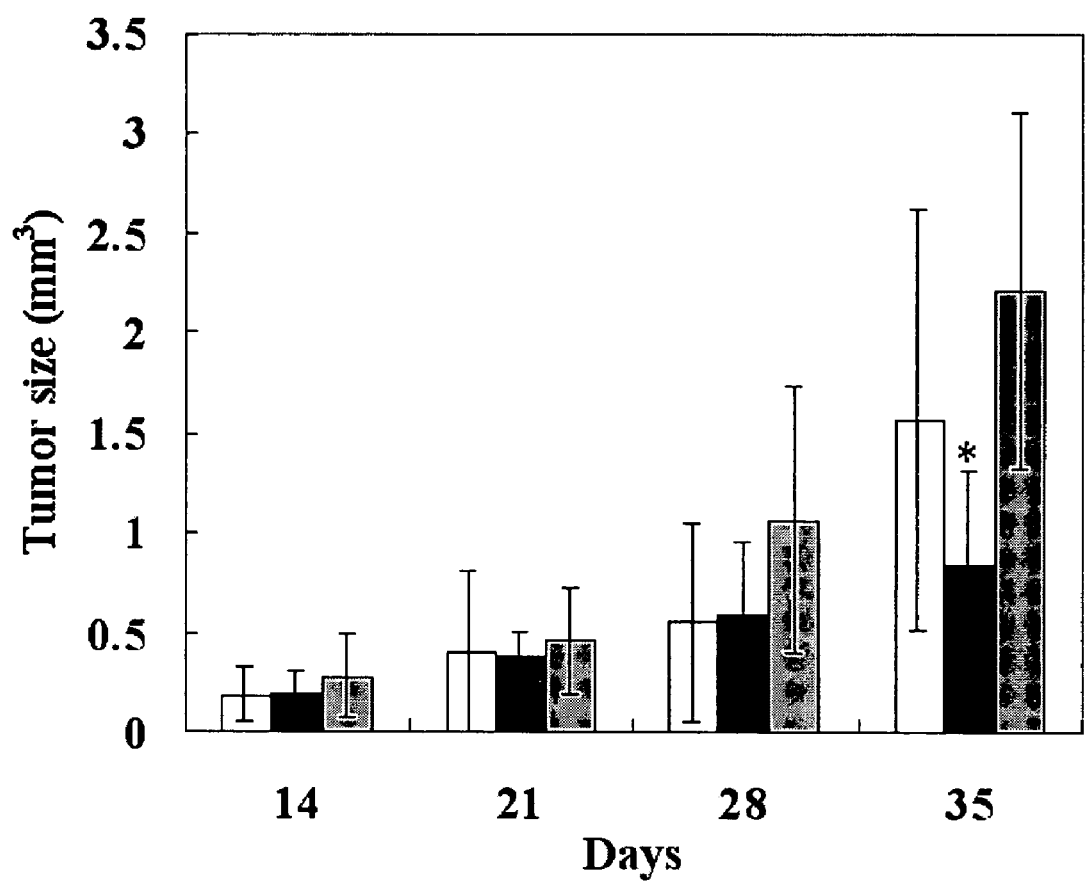
FIG. 9 shows in vivo tumor growth assay of TM-expressed A2058 melanoma cells.

To assess the functional consequences of TM-mediated adhesion, we next investigated whether the observed effects of TM-mediated adhesion could also affect the growth of A2058 tumor cell lines. TMG-, TMG(ΔL)-, or GFP-expressed cells were used to initiate tumors in SCID mice. The tumors induced by inoculation with TMG(ΔL)-expressed cells had about a 1.4 fold increased size, relative to the tumors induced by the GFP-expressed cells (FIG. 9). The tumors induced by the TMG-expressed cells have the smallest size in comparison to other transfected cells.

Discussion

Thrombomodulin (TM), which is a well-known anticoagulation factor, may function as a cell adhesion molecule, given that the glycoprotein is present in the junction of different epithelial cells (Tezuka, Y. et al., (1995) Cancer Res. 55, 4196–4200; Tabata, M., et. al., (1997) J. Oral. Pathol. Med. 26, 258–264 and Ogawa, H., et al. (2000) Cancer Lett. 149, 95–103). This role for TM was investigated in the present study. We utilized the A2058 cell line, which has no endogenous expression of TM or E-cadherin. A2058 cells were transfected with different constructs of TM genes to investigate the functions of TM and its domains in cell-cell adhesion and cell morphology. A2058 cells without TM assumed a fibroblastic-like cell morphology and were dispersed as single cells in cultures of non-confluent cell densities. In the clones of TMG, the green fluorescence-tagged TM was located at the cell surface, especially near the cell-cell junctions. Interestingly, the transfected cells assumed an epithelial-like morphology and formed sheet-like colonies with obvious cell-to-cell adhesion in the culture (FIG. 2). In contrast, the clones of TMG(ΔL)-expressed cells displayed fibroblastic-like morphology with less adhesion observed. The results indicate that TM acts as a cell-cell adhesion molecule. Adhesion molecules, in particular E-cadherin, have also been reported to cause morphological transition, for example, from the fibroblastic cell type to the epithelial cell type of several cell lines (Takeichi, M. (1991) Science 251, 1451–1455; Pignatelli, M. et al., (1992) Br J. Cancer 66, 629–634; and Togasgi, H. et al., (2002) Neuron. 35, 77–89). In the TMG transfected A2058 cells, E-cadherin could not be detected by immunohistochemical staining (data not shown). In this study, TM appears to assume the function typically attributed to E-cadherin.

Figure 6:
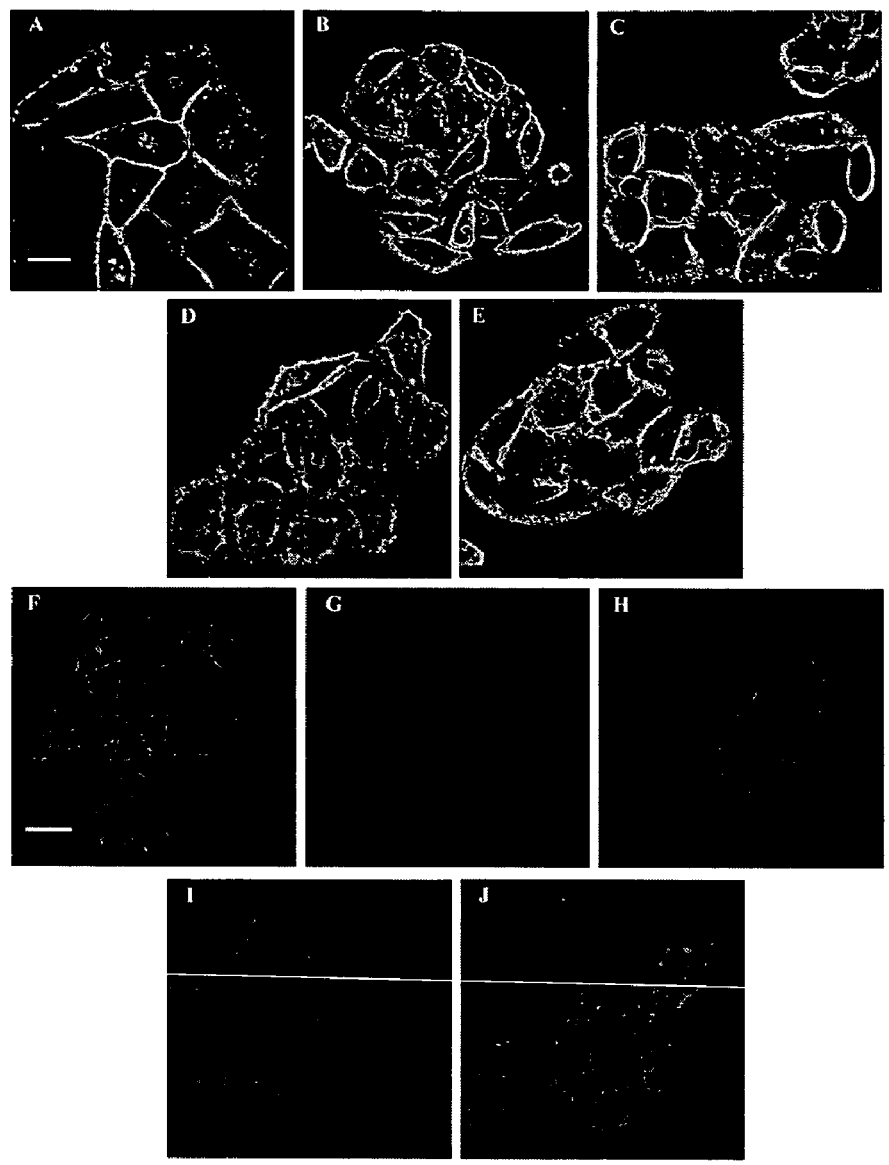
FIG. 6 shows TM participates in $Ca^{2+}$-dependent cell-cell adhesion.

Lectins represent a diverse category of carbohydrate binding proteins (including C, P, and I-types). Among these distinct types of lectins, the C-type lectins are distinguished by their requirement for $Ca^{2+}$ for sugar binding (Mody, R., et al. (1995) J. Pharmaco. Toxicol. Meth. 33, 1–10). Biological functions of the lectin-like domain unrelated to the anticoagulatant activity of TM that have been proposed include internalization of TM-thrombin complex (Conway, E. M., et. al., (1997) Blood 89, 652–661), regulation of cell proliferation (Zhang, Y., et al. (1998) J. Clin. Invest. 101, 1301–1309), and interference with the adhesion of polymorphonuclear leukocytes (PMN) to activated endothelial cells (Conway, E. M., et. al., (2002) J. Exp. Med. 196, 565–577). Presently, we provide several lines of evidence to demonstrate that the TMG lectin-like domain may be directly involved in cell-to-cell interaction. Firstly, only the culture of TMG-transfected A2058 cells formed close cell-cell contacts, not the culture of parental or TMG(ΔL) cells (FIGS. 2 and 3). Secondly, the cell-cell adhesion in TMG-expressed cells is $Ca^{2+}$-dependent, since cell association could be blocked by EGTA, and was restored by $Ca^{2+}$ (FIG. 6). The observation reveals that lectin-like domain of TM is a C-type lectin. Furthermore, this restoration of cell-cell adhesion can be blocked by anti-lectin-like domain antibody, consistent with the proposed function of TM. Thirdly, anti-lectin-like domain antibody, not the anti-EGF-like domain antibody, is able to block cell-to-cell contacts and inhibit the close clustering morphology in TMG cells (FIG. 3). In the A2058 cell line, no E-cadherin was expressed and anti-E-cadherin antibody could not block the cell-cell adhesion (FIG. 6E). Fourthly, it is noteworthy that the infiltration rate of protein molecules has been decreased to 40–50% in the TMG cell monolayer (FIG. 4). Such a shift in protein permeability suggests that TM might be either a mediator of cell-cell contacts or a molecule directing the establishment and the maintenance of the cell-cell adhesion. Finally, analysis of possible carbohydrate ligands showed that mannose, or chondroitin sulfate (including A and C), blocked the cell-to-cell adhesion in TMG cells. The results provided more detailed evidence concerning the function of lectin-like domain in the TM-mediated cell-cell adhesion. Taken together, these observations prompt us to propose that lectin-like domain in TMG-transfected A2058 cells mainly mediate cell-cell adhesion by $Ca^{2+}$-dependent binding to its specific carbohydrate ligands on the neighboring cells.

Adherens junction is a specialized form of cadherin-based adhesive contacts required for epidermal sheet organization. E-cadherin is expressed throughout the epidermis and has been identified as one of major adherens junction molecules mediating keratinocyte-keratinocyte interaction. Specific antibodies inhibiting its function cause severe perturbations in normal skin structure (Hirano, S. et. al., (1997) *J. Cell. Biol.* 105, 2501–2510). Similarly, TM antigen was reported to be lost in blistering dermatoses, implying that TM may also participate in cell-cell adhesion in epidermis.

To verify the participation of TM in cell adhesion, we investigated the perturbing effect on the cell-cell adhesion of HaCaT by incubating the cells with anti-TM and anti-E-cadherin antibodies. In this spontaneously transformed keratinocyte cell culture, both TM and E-cadherin are detected on the cell membrane, especially with high concentration at cell-cell junctions. As shown in FIG. 6, either the anti-lectin-like domain antibody or anti-E-cadherin antibody could inhibit $Ca^{2+}$-induced cell-cell re-adhesion of EGTA-treated HaCaT cells. It appears that both E-cadherin and TM are necessary for the formation of cell junctions in HaCaT cell lines. We were able to further evidence this hypothesis through the characterization of TM distribution during cell-cell adhesion disruption. When HaCaT cells were treated with EGTA, TM became clearly disorganized and intracellular localized (FIG. 6I), consistent with the involvement of TM in the scaffolding of adhesion molecules at the lateral membrane during events of cell-cell adhesion formation or disruption. Furthermore, we have noted similar staining patterns between TM and E-cadherin on HaCaT cells (data not shown). Blockage of the function of either one of these two potential adhesive molecules will cause the cells incapable to form cell-cell attachment at least in the time period. A functional hierarchy in the assembling of cell-cell adhesion by these two adhesion molecules is on the current investigation.

Figure 7:
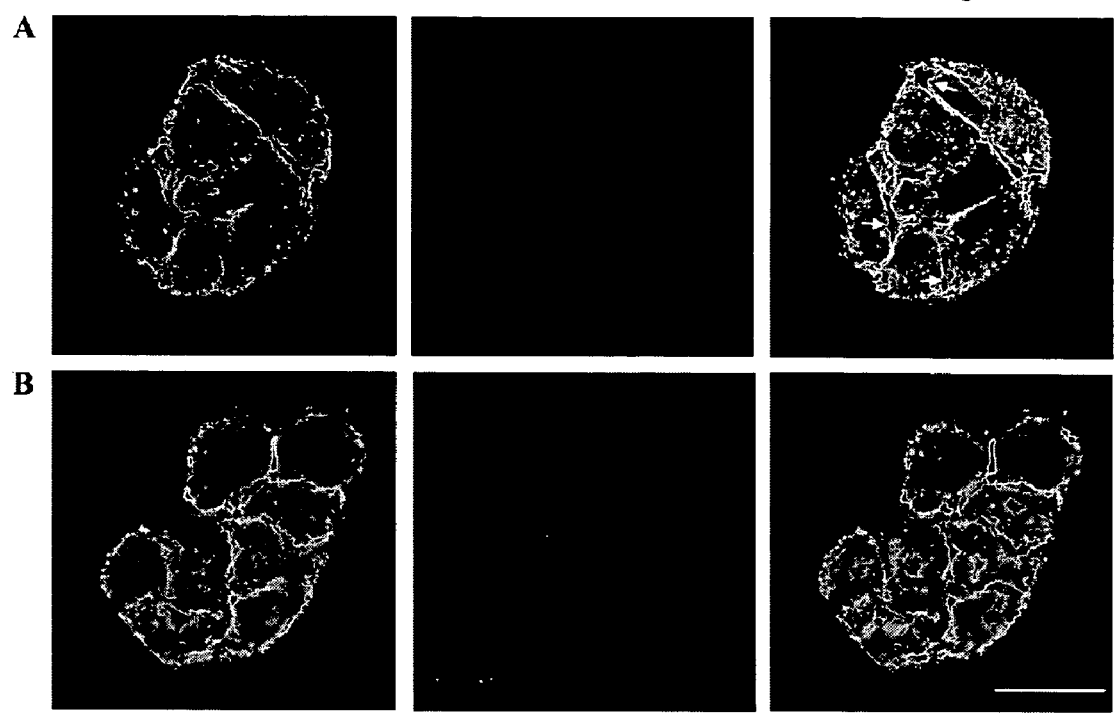
FIG. 7 shows colocalization of TM (green) and the actin (red) in TMG-expressed cells.

It is important to identify the physiological ligands of the C-type lectin-like domain of TM to fully understand the functional significance and mechanism of TM in the cell-cell adhesion. Adhesion molecules such as cadherins prefer to bind themselves through homotypic interactions, whereas molecules of the immunoglobulin-cell adhesion molecule family (Ig-CAM) bind cell surface proteins via heterotypic interactions (Hubbard, A. K. et. al., (2000) *Free. Rad. Biol. Med.* 28, 1379–1386). The ligands of some endogenous lectins have been recognized, including sialyl-Lewisx, sialyl-Lewisa, sulfated polysaccharides, and the mannose-6-phosphate-containing polysaccharides (Steven D. Rosen (2004) *Annu. Rev. Immunol.* 22:129–56; Varki, A. et. al., (2001) *Braz. J. Med. Biol. Res.* 34, 711–717; and Stahl, P. D. (1992)*Curr. Opin. Immunol.* 4, 49–52). However, the ligand of lectin-like domain of TM has never been identified. The present study reveals that the lectin-like doamain of TM can bind carbohydrates. The candidate carbohydrates contain mannose residue, chondroitin sulfate A, or chondroitin sulfate C moieties, though mannose showed the highest dispersing effect. Although previous studies reported TM contained mainly chondroitin sulfate A (chondroitin 4-sulfate) (Nawa, K, et. al., (1990) *Biochem. Biophys. Res. Commun.* 171, 729–737), we found that the same concentration of chondroitin sulfate C (chondroitin 6-sulfate) also dispersed the clustering colonies. Unlike chondroitin sulfate, mannose was broadly existed in carbohydrate moiety of glycoproteins or glycolipids (Pollack, L. et. al., (1983) *J. Cell. Biol.* 97, 293–300). This result suggests that mannose could be one of the ligands of lectin-like domain. However, we cannot rule out the possibilities that the carbohydrate ligands of TM lectin-like domain belong to the glycoconjugated molecules on cell surface other than TM. The structure of the nature carbohydrate ligands still remained to be identified. The interaction of cytoplasmic domain of adhesion molecules and cytoskeleton also has been demonstrated to be essential for cell-cell adhesion. These interactions could provide adhesion strength in endothelial or epithelial sheets, allowing them to resist mechanical disruption (Pokutta, S., et. al., (2002) *Curr. Opin. Struct Biol.* 12, 255–262). Presently, we observed that the TMG protein and actin molecules were colocalized in the cortex region of the cells (FIG. 7). The culture cells with cytoplasmic domain-truncated TM did not form close-clustering colonies (unpublished results). The results indicate that the cytoplasmic domain of TM is necessary in forming stable cell-to-cell adhesion. One of the possible functions of the cytoplasmic domain is that it may associate with actin through uncharacterized linkage proteins that regulate TM distribution on the cell surface as cadherin (Kinch, M. S. et. al., (1995) *J. Cell. Biol.* 130, 461–471). However, transgenic mice lacking of TM $NH_2$-terminal lectin-like domain (Conway, E. M. et. al., (2002) *J. Exp. Med.* 196, 565–577) or cytoplasmic domain of TM (Conway, E. M. et. al., (1999) *Blood* 93, 3442–3450) were found to have normal fetal development. It is possible that in animal tissues other potential molecules such as cadherins may compensate the loss of adhesive function of the truncated TM domains (Takeichi, M. et. al., (1991) *Science* 251, 1451–1455). The physiological significance of TM-mediated cell-cell adhesion remained to be further investigated in vivo.

The down-regulation of E-cadherin expression has been documented in the cells of poorly differentiated tumors, indicating that a decrease in cell-cell adhesion may be associated with undifferentiated phenotype and aberrant growth of tumors (Conacci-Sorrell, M. et. al., (2002) *J. Clin. Invest.* 109, 987–991). Similarly, the inverse relationship of TM expression and cell proliferation rate has been reported in hepatocellular carcinoma, ovarian carcinoma, and esophageal squamous carcinoma (Tezuka Y. et al., (1995) *Cancer Res.* 55, 4196–4200; Tabata, M., et al., (1997) *J. Oral. Pathol. Med.* 26, 258–264 and N. G. Ordóñez (2000) Histopathology 36, 433–438). The parallel correlation between E-cadherin and TM in tumor progress implies that less cell-cell adhesion maybe involved in tumor progression and the onset of an invasive phenotype of carcinomas.

In order to prove the invention that TM-induced cell-cell adhesion may affect the tumor growth rate in vivo, the tumor growth rates were measured in SCID mice following inoculation of TMG- or TMG(ΔL)-expressed A2058 cells. Tumor size was greatest in tumors arising from TMG(ΔL)-expressed cells, intermediate in vector, and lowest in TMG-expressed cells (FIG. 9). The results show that TMG without the lectin-like domain lack the restrain activity in cell proliferation. We therefore suggested that the increase of cell-to-cell adhesion upon TM expression may slowdown tumor growth in vivo.

It confirms that TM could be present as a multifunctional molecule. It not only can function as an anticoagulant regulator in the vascular endothelial cells, it may also function as a cell-cell adhesion molecule through a $Ca^{2+}$-dependent interaction of lectin-like domain.

DETAILED DESCRIPTION OF FIGURES

FIG. 1. (A) Schematic diagram illustrating TMG and TMG(ΔL) constructed in pEGFPN1. Nascent human TM consists of 575 amino acid residues beginning with a putative 18-residue signal peptide (SP) at the N-terminal end. SP, followed by 5 structural domains: $NH_2$-terminal lectin-like domain, (including hydrophobic region (HP); Six EGF-like repeats; serine/threonine (SerThr)-rich region; transmembrane (tm) domain; and, cytoplasmic tail (cyt). cDNA constructs of the full length or lectin-like domain-deleted TM were transfected into A2058 cells for expression of TMG or TMG(ΔL). (B) TM activity assay of A2058 cells stably expressing TMG and TMG(ΔL). Confluent monolayers of A2058cells (A), GFP control (x), TMG (O) and TMG(ΔL) (♦) were assayed for TM-dependent protein C activation activity as described in the Experimental Procedures. The change in absorbance at 405 nm was monitored. (C) Characterization of TM proteins by mouse anti-human TM antiserum. Ten □g of cell lysates were subjected to SDS-polyacrylamide gel electrophoresis followed by electrotransfer onto filters and blotting with mouse anti-human TM antiserum. Positions and apparent molecular mass standards (in kDa) are shown as indicated. Western blot results from A2058 cells transfected with GFP (lane 1), TMG (lane 2), and TMG(ΔL) (lane 3) are shown.

FIG. 2. Confocal microscopy examination of the subcellular distribution of TM proteins in A2058 cells and the cell morphology. Confocal microscopy was utilized to observe A2058 cells stably expressing GFP (A), TMG (B), and TMG(ΔL) (C). The cells were fixed and photographed to observe the localization of TM protein. Bar, 40 μm.

FIG. 3. Effects of anti-TM antibodies on the organization of cell-cell adhesion junctions in TMG-expressed A2058 cells. Anti-lectin-like domain antibody (10 μg/ml) or isotype-matched control IgG (10 μg/ml) was added to cultured monolayers for 24 h (A), and the cell morphology was examined using a Leica inverted microscope. A comparative morphology of the TMG-expressed cells treated with anti-EGF-like domain antibody (10 μg/ml) was photographed (B).

FIG. 4. Overexpression of TMG decreases the A2058 cell monolayer permeability. Monolayer cell permeability was decreased in A2058 cells overexpressing TMG as determined by HRP flux across confluent monolayer. Statistical evaluation of quadruplicate determinations showed a statistically significant between TMG (■) and TMG(ΔL) (▨) or GFP-expressed control (□). *$p<0.05$ vs. GFP-expressed cells. Unpaired Student's t-test was used. The experiment was repeated three times.

Figure 5:
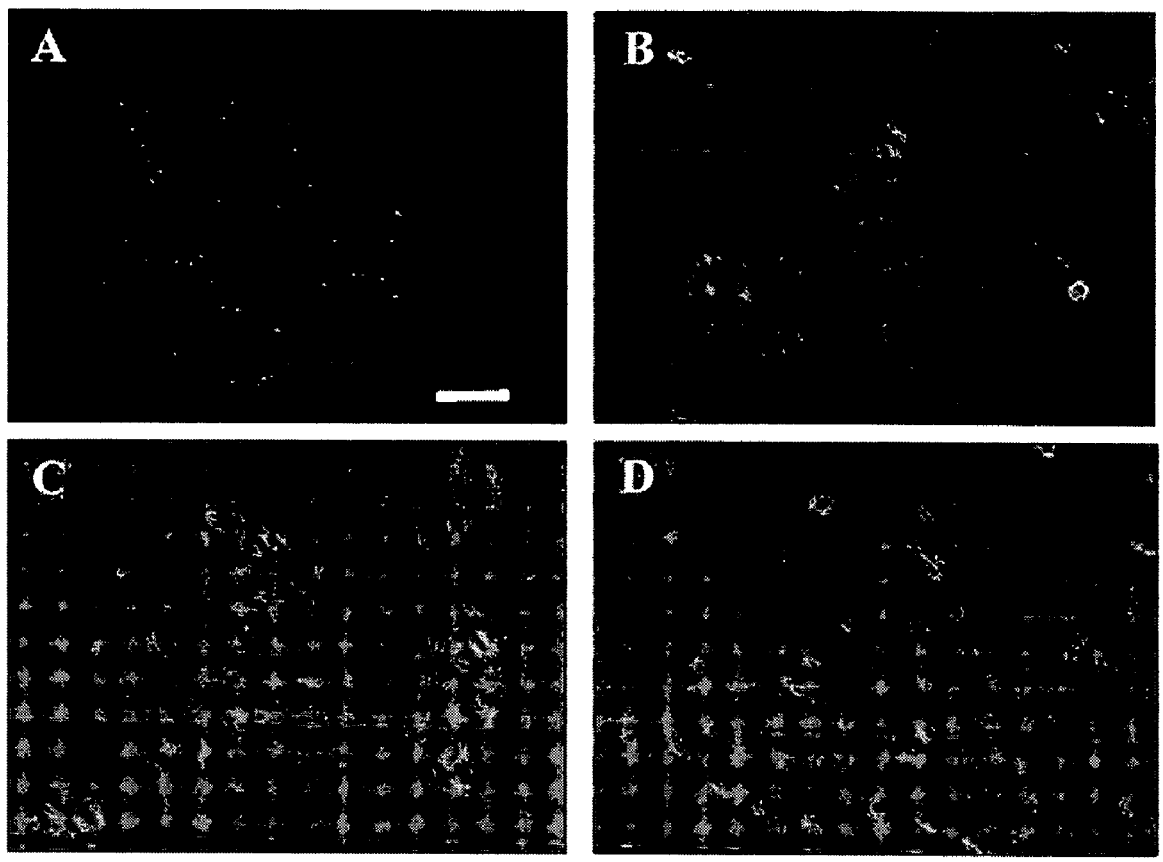
FIG. 5 shows localization of TM protein and effects of anti-TM antibodies on the cell-cell adhesion of HaCaT cell's.

FIG. 5. Localization of TM protein and effects of anti-TM antibodies on the cell-cell adhesion of HaCaT cells. HaCaT cells were incubated with anti-lectin-like domain of TM antibody and detected with tetramethylrhodamine-conjugated anti-mouse antibody. Cells were photographed by confocal microscopy. Bar, 40 μm. (A). HaCaT cells were treated with 10 μg/ml of isotype-control IgG (B), 10 μg/ml anti-EGF-like domain antibody (C), or 10 μg/ml anti-lectin-like-domain antibody (D) for 24 h. Cells were photographed by a Leica inverted microscope. The results shown are representative of three independent experiments.

FIG. 6. TM participates in $Ca^{2+}$-dependent cell-cell adhesion. A2058TMG (A–E) and HaCaT cells (F–J) were left untreated (A, F) or treated with 4 mM EGTA for 40 min (B–E, G–J). The EGTA containing medium was then replaced with $Ca^{2+}$-containing medium in the presence of 10 μg/ml control IgG (C, H) for 1 h. After treatment with EGTA, cells were incubated for 1 h in medium containing 1.8 mM $Ca^{2+}$ and 10 □g/ml function-blocking anti-lectin-like antibody (D, I), or anti-E-cadherin antibody (E, J). Green fluorescence shown in panels A to E is the GFP-tagged TM proteins, whereas panels F to J indicate the TM distribution by anti-EGF-like domain antibody detected with tetramethylrhodamine-conjugated anti-mouse antibody. Bar, 40 μm.

FIG. 7. Colocalization of TM (green) and the actin (red) in TMG-expressed cells. TMG-expressed cells were fixed, permeabilized and immunolocalized using tetramethylrhodamine-conjugated phalloidin (A) or a monoclonal antibody recognizing human keratin (B). The merge panel shows the superimposed images from TMG and tetramethylrhodamine fluorophore. Three separate experiments produced similar results. The arrows denote the colocalization of TM and actin filaments. Bar, 20 μm.

Figure 8:
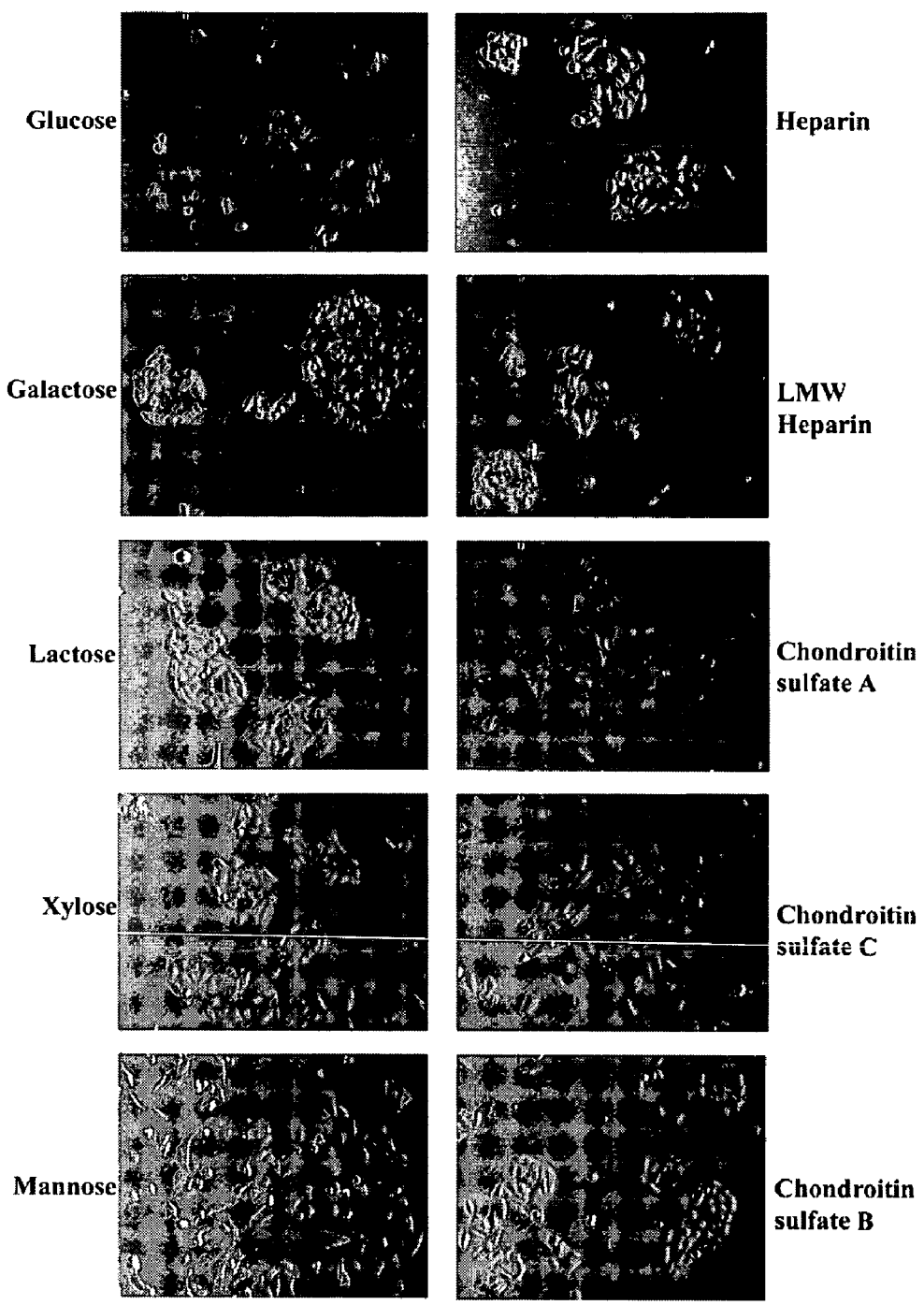
FIG. 8 shows effect of different carbohydrates on the cell adhesion of TMG cells.

FIG. 8. Effect of different carbohydrates on the cell adhesion of TMG cells. TMG-expressed A2058 cells were challenged with 20 mg/ml of monosaccharides (including D-glucose, D-galactose, D-lactose, D-xylose, D-mannose), 20 mg/ml of chondroitin sulfate A, B, C, or 15 mg/ml of heparin, LMW heparin. Following incubation at 37° C. overnight, images were obtained. Each image is representative of the observations from three separate experiments.

FIG. 9. In vivo tumor growth assay of TM-expressed A2058 melanoma cells. A total of $1\times10^6$ TMG (■)-, TMG(ΔL)(▨)- or GFP (□)-expressed cells was injected subcutaneously into SCID mice. Tumor size was recorded every 7 days by measuring the two largest diameters. Data show mean±SD of five tumors in each group, and the experiment was repeated three times independently. *$p<0.05$ vs. GFP-expressed cells. Unpaired Student's t-test was used.

While the invention has been described and exemplified in sufficient detail for those skilled in this art to make and use it, various alternatives, modifications, and improvements should be apparent without departing from the spirit and scope of the invention.

One skilled in the art readily appreciates that the present invention is well adapted to carry out the objects and obtain the ends and advantages mentioned, as well as those inherent therein. The cell lines, embryos, animals, and processes and methods for producing them are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations, which are not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

We claim:

1. A composition comprising thrombomodulin and a substance binding the lectin-like domain of thrombomodulin selected from the group consisting of mannose, mannose oligomer, mannose polymer, mannose analogues, mannose complex molecules, chondroitin sulfate, chondroitin sulfate oligomer, chondroitin sulfate polymer, chondroitin sulfate analogues and chondroitin sulfate complex molecules.

2. The composition according to claim 1 wherein thrombomodulin functions as a $Ca^{2+}$-dependent cell-to-cell adhesion molecule.

3. The composition according to claim 1 wherein the substance binding the lectin-like domain of thrombomodulin is selected from the group consisting of mannose, chondroitin sulfate A and chondroitin sulfate C.

4. The composition according to claim 1 further comprising at least one selected from the group consisting of a drug, peptide, compound, DNA, and RNA for cosmetic or therapeutic use.

5. The composition of claim 1 wherein the substance binding the lectin-like domain of thrombomodulin is ligated to a matix or a solid surface.

* * * * *

SEQUENCE LISTING

```
<160> NUMBER OF SEQ ID NOS: 5

<210> SEQ ID NO 1
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 1
cgggatcccg gaatgcttgg ggtcctggtc cttg                                34

<210> SEQ ID NO 2
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 2
ggaattcgga gtctctgcgg cgtccgct                                       28

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 3
cattgcacgc gtgctcgcag ccgc                                           24

<210> SEQ ID NO 4
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 4
cacgctgcag tcccaagcgc cacccggctg cggctc                              36

<210> SEQ ID NO 5
```

```
-continued

<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 5
gagccgcagc cgggtggcgc ttgggactgc agcgtg                               36
```